US00PP11744P2

(12) United States Plant Patent
VandenBerg

(10) Patent No.: US PP11,744 P2
(45) Date of Patent: Jan. 23, 2001

(54) CHRYSANTHEMUM PLANT NAMED 'SIBILA'

(75) Inventor: Cornelis P. VandenBerg, Salinas, CA (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/245,659

(22) Filed: Feb. 8, 1999

(51) Int. Cl.[7] ..... A01H 5/00
(52) U.S. Cl. ..... Plt./287

(58) Field of Search ..... Plt./286, 287, 292

*Primary Examiner*—Howard J. Locker
(74) *Attorney, Agent, or Firm*—C. A. Whealy

(57) ABSTRACT

A distinct cultivar of Chrysanthemum plant named 'Sibila', characterized by its decorative spray-type inflorescences that are about 6.8 cm in diameter; attractive lavender pink ray florets; numerous inflorescences per stem; numerous ray florets per inflorescence; uniform flowering; and excellent postproduction longevity with inflorescences maintaining good substance and color for about four weeks in an interior environment after one week of cool storage.

2 Drawing Sheets

BACKGROUND OF THE INVENTION

The present invention relates to a new and distinct cultivar of Chrysanthemum plant, botanically known as *Dendranthema grandiflora* and referred to by the cultivar name Sibila.

The new Chrysanthemum is a product of a planned breeding program conducted by the Inventor in Salinas, Calif. The objective of the breeding program is to create new cut Chrysanthemum cultivars having inflorescences with desirable colors and good form and substance.

The new Chrysanthemum originated from a cross made by the Inventor in January, 1993, in Salinas, Calif., of a proprietary Chrysanthemum seedling selection identified as 1841 as the female, or seed, parent with a proprietary Chrysanthemum seedling selection identified as 1092, as the male, or pollen, parent.

The cultivar Sibila was discovered and selected by the Inventor as a flowering plant within the progeny of the stated cross in a controlled environment in Alva, Fla., in April, 1994. The selection of this plant was based on its desirable inflorescence color and good form and substance.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Sibila has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sibila'. These characterstics in combination distinguish 'Sibila' as a new and distinct cultivar:

1. Decorative spray-type inflorescences that are about 6.8 cm in diameter.
2. Attractive lavender pink ray florets.

3. Numerous inflorescences per stem.
4. Numerous ray florets per inflorescence.
5. Uniform flowering.
6. Excellent postproduction longevity with inflorescences maintaining good substance and color for about four weeks in an interior environment after one week of cool storage.

BRIEF DESCRIPTION OF THE PHOTOGRAPHS

The accompanying colored photographs illustrate the overall appearance of the new Chrysanthemum, showing the colors as true as it is reasonably possible to obtain in colored reproductions of this type.

The photograph on the first sheet comprises a side perspective view of a typical flowering stem of 'Sibila' grown as a spray-type cut Chrysanthemum.

The photograph at the top of the second sheet comprises a top perspective view of typical inflorescences of the cultivar Sibila.

The photograph at the bottom of the second sheet comprises a close-up view of upper (left side of photograph) and lower (right side of photograph) surfaces of typical inflorescences (top of photograph) and typical leaves (bottom of photograph) of the cultivar Sibila. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Madrid, Cundinamarca, Colombia, under commercial practice in a single-layer polyethylene-covered greenhouse. Plants were planted on May 6, 1998 and received 14 long day/short nights followed by short day/long nights until flowering. During the production time, the following environmental conditions were measured: day temperatures ranging from 24 to 38° C.; night temperatures ranging from 6 to 10° C.; and accumulated solar energy ranging from 16 to 27.6 KWH/$m^2$. Measurements and numerical values represent averages for six to ten typical flowering stems.

Botanical classification: *Dendranthema grandiflora* cultivar Sibila.

Commercial classification: Decorative spray-type cut Chrysanthemum.

Parentage:

*Male or pollen parent.*—Unnamed proprietary *Dendranthema grandiflora* seedling selection, code number 1841.

*Female or seed parent.*—Unnamed proprietary *Dendranthema grandiflora* seedling selection, code number 1092.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative spray-type cut flower. Stems upright, uniform habit and freely branching.

*Flowering stem length.*—About 104 cm.

*Stem color.*—147B.

*Stem texture.*—Pubescent.

*Foliage description.*—Arrangement: Alternate. Length: About 9.2 cm. Width: About 5.7 cm. Apex: Cuspidate. Base: Attenuate. Margin: Palmately lobed; sinuses, parallel to convergent with some overlapping. Texture: Upper and lower surfaces slightly pubescent. Veins prominent on lower surface. Color: Young foliage upper surface: 147A. Young foliage lower surface: Slightly darker than 147B. Mature foliage upper surface: 147A. Mature foliage lower surface: 147B. Venation upper surface: 147B. Venation lower surface: 147B. Petiole: Length: About 2.2 cm. Diameter: About 2.5 mm. Color: 147B–147C.

Flowering description:

*Appearance.*—Decorative spray-type inflorescence form with oblong-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 65 days later.

*Postproduction longevity.*—In an interior environment, flowering stems will maintain good color and substance for about four weeks in an interior environment after one week of cool storage.

*Quantity of inflorescences.*—About 9 inflorescences per flowering stem.

*Inflorescence size.*—Diameter: About 6.8 cm. Depth (height): About 2.3 cm. Diameter of disc: About 4 mm.

*Ray florets.*—Shape: Oblong. Length: About 3.5 cm. Corolla tube length: About 3.5 mm. Width: About 1 cm. Apex: Rounded or dentate. Base: Tubular, short corolla tube. Margin: Entire. Texture: Satiny, smooth, glabrous; ridged longitudinally. Surface: Initially concave, then flattened to convex. Aspect: Initially upright then perpendicular to peduncle. Number of ray florets per inflorescence: About 189. Color: When opening: Initially white then 70A–70B. Mature: Upper surface: 75A, iridescent; white at base. Lower surface: 75A to 75D; white at base.

*Disc florets.*—Shape: Tubular. Length: About 6 mm. Width: About 1 mm. Number of disc florets per inflorescence: About 12. Color: Immature: 154A. Mature: Apex: 13A–15A. Base: White.

*Peduncle.*—Aspect: Strong and angled about 30° to the stem. Length: First peduncle: About 8.6 cm. Fourth peduncle: About 13.4 cm. Seventh peduncle: About 18.3 cm. Texture: Very fine pubescence. Color: 147B.

*Reproductive organs.*—Androecium: Present on disc florets only. Anther color: 14A. Amount of pollen: Scarce. Gynoecium: Present on both ray and disc florets.

Disease resistance: Resistance to diseases common to Chrysanthemums has not been observed on plants grown under commercial conditions.

Seed production: Seed production has not been observed.

It is claimed:

1. A new and distinct cultivar of Chrysanthemum plant named 'Sibila', as illustrated and described.

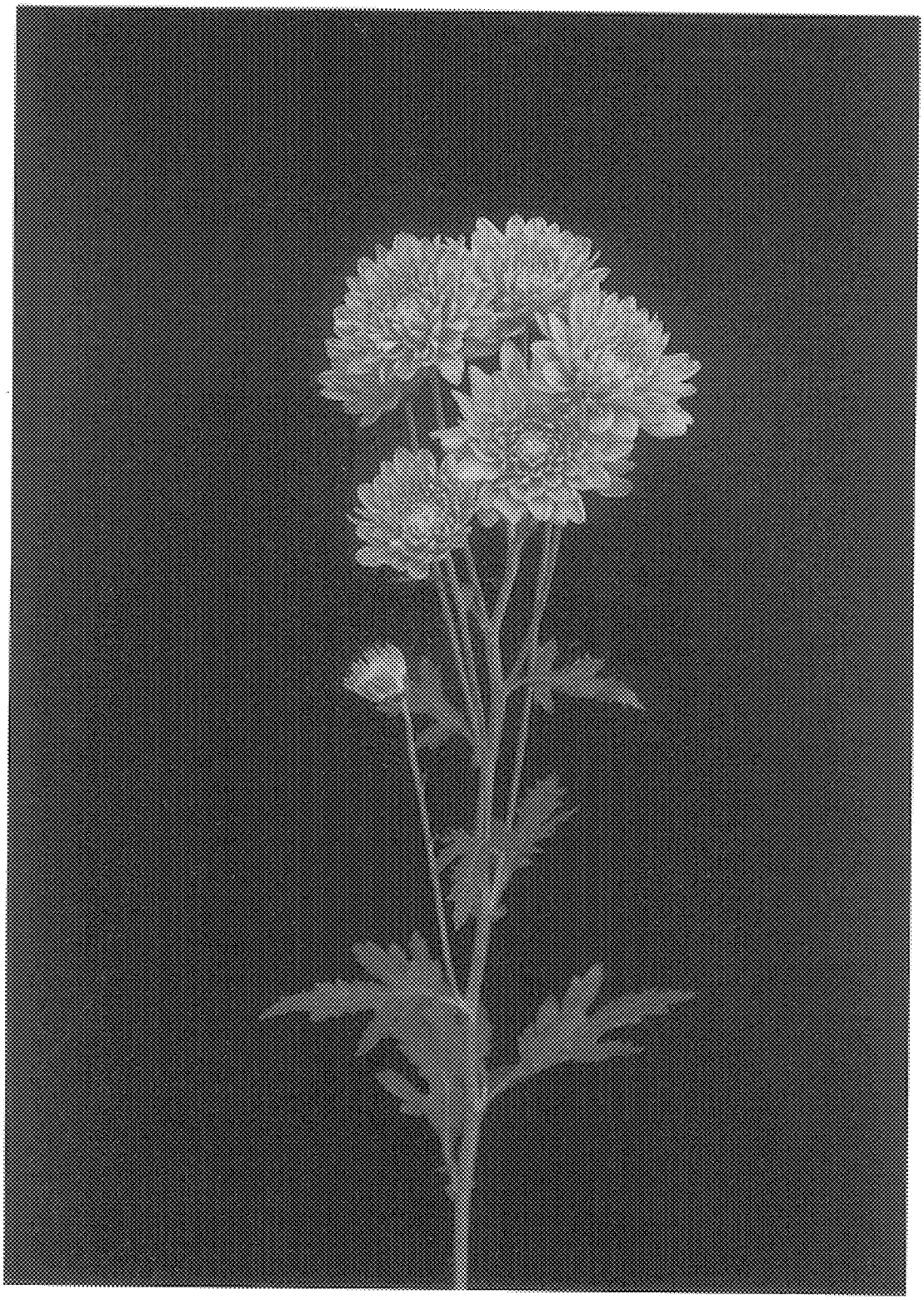

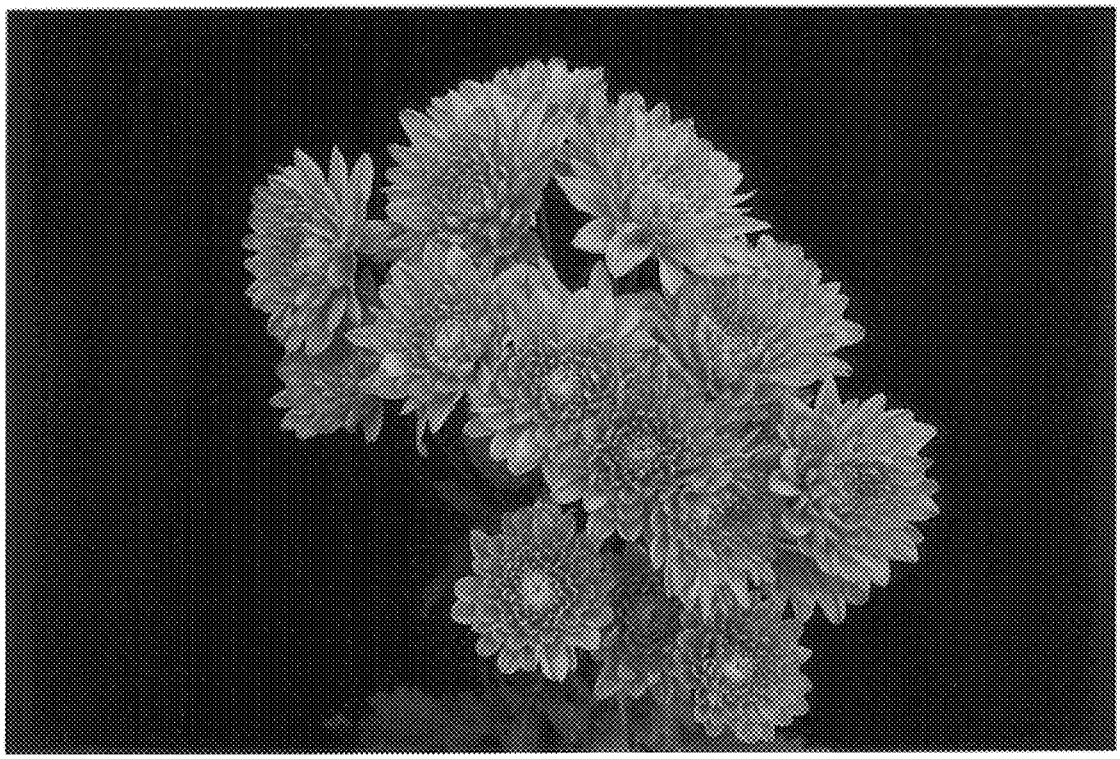
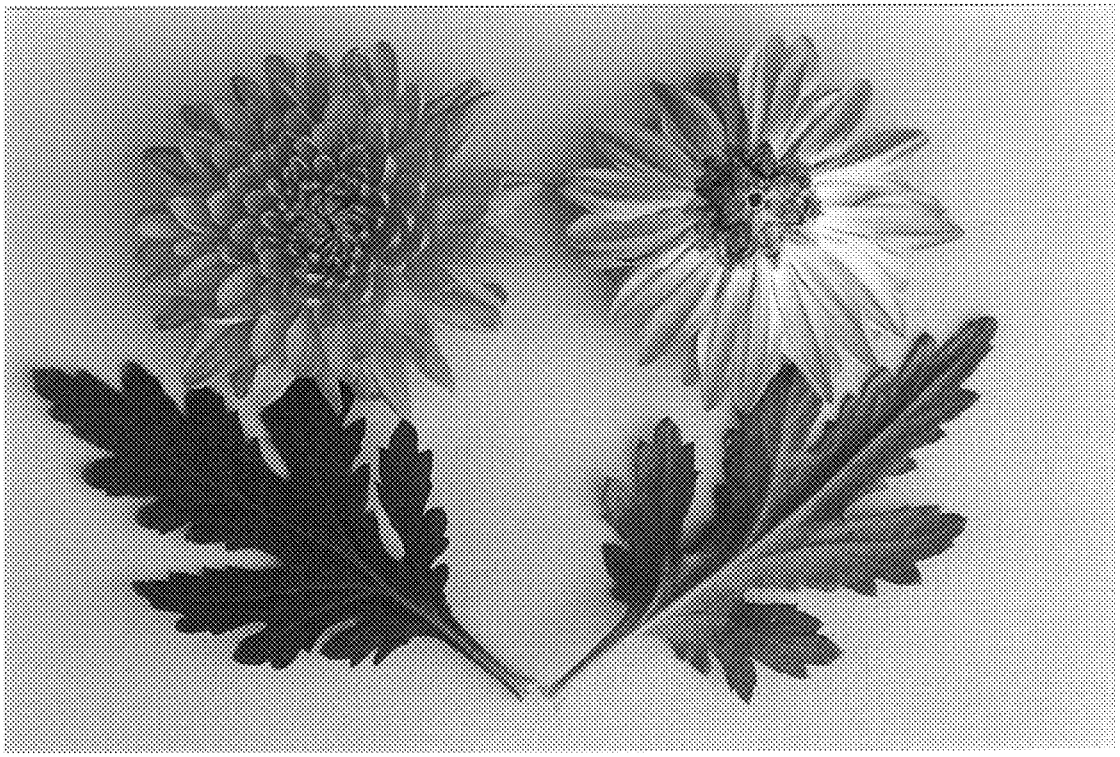

* * * * *